(12) United States Patent
Christoph et al.

(10) Patent No.: US 8,804,905 B2
(45) Date of Patent: Aug. 12, 2014

(54) COORDINATE MEASURING APPARATUS AND METHOD FOR MEASURING AN OBJECT

(75) Inventors: Ralf Christoph, Gießen (DE); Wolfgang Rauh, Waldenbuch (DE)

(73) Assignee: Werth Messtechnik GmbH, Giessen (DE)

(*) Notice: Subject to any disclaimer, the term of this patent is extended or adjusted under 35 U.S.C. 154(b) by 161 days.

(21) Appl. No.: 11/597,625

(22) PCT Filed: May 24, 2005

(86) PCT No.: PCT/EP2005/005598
§ 371 (c)(1), (2), (4) Date: Nov. 27, 2006

(87) PCT Pub. No.: WO2005/119174
PCT Pub. Date: Dec. 15, 2005

(65) Prior Publication Data
US 2008/0075227 A1    Mar. 27, 2008

(30) Foreign Application Priority Data

May 26, 2004 (DE) .......................... 10 2004 026 357
Oct. 14, 2004 (DE) .......................... 10 2004 050 257
Apr. 20, 2005 (DE) .......................... 10 2005 018 447

(51) Int. Cl.
*G01N 23/083* (2006.01)
*G01N 23/04* (2006.01)
*A61B 6/00* (2006.01)
*G01B 15/04* (2006.01)

(52) U.S. Cl.
CPC ............ *G01N 23/046* (2013.01); *G01N 23/083* (2013.01); *G01N 2223/3306* (2013.01); *G01N 2223/1006* (2013.01); *A61B 6/4417* (2013.01); *A61B 6/583* (2013.01); *G01B 15/04* (2013.01)

USPC .............................. 378/63; 378/19; 378/196

(58) Field of Classification Search
CPC . G01N 23/04; G01N 23/083; G01N 2223/03; G01N 2223/04; G01N 2223/10; G01N 2223/1006; G01N 2223/101; G01N 2223/1016; G01N 2223/308; G01N 2223/309; G01N 2223/32; G01N 2223/33; G01N 2223/3306; H05J 1/02; A61B 6/035; A61B 6/44; A61B 6/4417; A61B 6/4429
USPC .......... 378/4, 19, 51, 53–58, 62, 63, 95, 98.8, 378/195–198; 600/427
See application file for complete search history.

(56) References Cited

U.S. PATENT DOCUMENTS 5,038,371 A    8/1991  Janssen et al.
5,419,320 A *  5/1995  Kawaguchi et al. .......... 600/425
(Continued)

FOREIGN PATENT DOCUMENTS

DE    44 45 331    6/1996
DE    100 01 239   7/2001
(Continued)

*Primary Examiner* — Thomas R Artman
(74) *Attorney, Agent, or Firm* — Ladas & Parry LLP

(57) ABSTRACT

The invention relates to a coordinate measuring apparatus (110) for measuring an object (3), comprising an x-ray sensory mechanism as a first sensory mechanism that is provided with an x-ray source (10) and at least one x-ray sensor (7) which detects the x-rays, and a second sensory mechanism such as a tactile and/or an optical sensory mechanism (8, 11; 9) that can be placed in the x, y, and/or z direction of the coordinate measuring apparatus in relation to the object. In order to be able to easily measure also large-size test objects, the x-ray sensory mechanism (7, 10) can be positioned in the coordinate measuring apparatus (10) according to the second sensory mechanism (8, 11; 9).

73 Claims, 7 Drawing Sheets

(56) References Cited

U.S. PATENT DOCUMENTS

Figure 1:
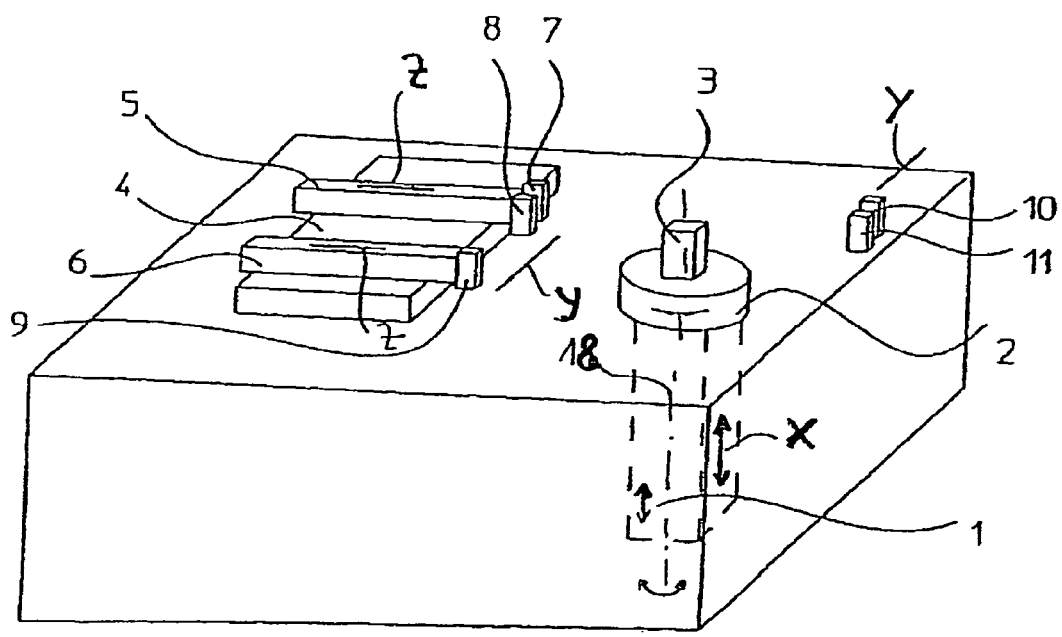

| | | | |
|---|---|---|---|
| 5,570,403 A * | 10/1996 | Yamazaki et al. | 378/5 |
| 5,725,632 A | 3/1998 | Kiss | |
| 5,764,721 A * | 6/1998 | Light et al. | 378/4 |
| 5,912,938 A * | 6/1999 | Dobbs et al. | 378/19 |
| 6,148,058 A * | 11/2000 | Dobbs | 378/19 |
| 6,470,068 B2 * | 10/2002 | Cheng | 378/20 |
| 6,611,575 B1 * | 8/2003 | Alyassin et al. | 378/37 |
| 6,614,875 B2 * | 9/2003 | Suuronen | 378/63 |
| 6,751,285 B2 * | 6/2004 | Eberhard et al. | 378/37 |
| 6,920,195 B2 * | 7/2005 | Ohishi et al. | 378/10 |
| 7,133,042 B2 * | 11/2006 | Anh et al. | 345/419 |
| 7,198,404 B2 * | 4/2007 | Navab et al. | 378/206 |
| 7,286,632 B2 * | 10/2007 | Yang et al. | 378/37 |
| 7,361,150 B2 * | 4/2008 | Berthonnaud et al. | 600/595 |
| 7,386,090 B2 * | 6/2008 | Schroeder et al. | 378/20 |
| 2003/0043964 A1 | 3/2003 | Sorenson | |
| 2006/0029181 A1 * | 2/2006 | Chen et al. | 378/17 |
| 2006/0239398 A1 * | 10/2006 | McCroskey et al. | 378/37 |

FOREIGN PATENT DOCUMENTS

| | | |
|---|---|---|
| DE | 103 31 419 | 1/2004 |
| EP | 0 504 691 | 9/1992 |
| GB | 740837 | 11/1955 |

\* cited by examiner

COORDINATE MEASURING APPARATUS AND METHOD FOR MEASURING AN OBJECT

This application is a 371 of PCT/EP2005/005598 filed on May 24, 2005.

The invention relates to a coordinate measuring device for measuring an object with an x-ray sensor system as the first part of the sensor system comprising an x-ray source, at least one x-ray sensor to measure the x-rays, and a shield against x-ray radiation; and a second sensor system, such as a tactile and/or optical sensor system, which can be positioned relative to the object along the x-, y- and/or z-axes of the coordinate measuring device. The invention also relates to a method for measuring an object comprising a coordinate measuring device with at least one x-ray sensor system as well as a method for calibrating the x-ray sensor system.

The use of coordinate measuring devices with various sensors for measuring the geometry of workpieces is known. These sensors are described as optical and tactile sensors (DE.Z: Die Bibliothek der Technik, Vol. 248). The use of computer-tomographs in determining workpiece geometry, particularly defects, is also known. DE-A-103 31 419 describes a combination of both of these devices. In this particular case, a computer-tomograph is fixedly secured to the basic assembly of the coordinate measuring device. Using classic coordinate measuring machine-sensor technology, the position of the object of measurement is determined and subsequently positioned in the measurement range of the computer-tomograph.

The described prior art does not deal with several problems. For example, the problem of an object of measurement potentially exceeding the measurement range of the computer-tomograph has not been solved. Because this component is fixedly secured to the basic assembly of the coordinate measuring device, a composite image made up of several computer-tomography images is not possible.

Furthermore, computer-tomographs usually have relatively gross measurement uncertainty in the magnitude of 10 µm or above. Measuring an object of measurement with computer-tomography alone—as described in DE-A 103 31 419—is therefore not sufficient for the complete solution of geometrical measuring tasks involving conventional customized parts. An additional problem is the geometric calibration of computer-tomographs. Because the characteristics of tomographic measurement strongly depend on the characteristics of the measuring object itself, calibration is possible only by means of a difficult and comprehensive procedure involving measurement standards.

From DE-A-100 44 169, a method for determining the thickness of workpieces is known. In this example, the x-rays penetrating a component to be measured strike a detector. With the aid of a manipulator, the component can be turned as well as raised and lowered. Following the complete transillumination of the component, the computer of a computer-tomograph transmits a batch of grayscale sectional images, which are then assembled to create a three-dimensional voxel-dataset. The wall thickness of the component is then calculated from this information.

DE-C-38 06 686 describes a coordinate measuring device with a multisensor sensing system that comprises a tactilely functioning sensor, a laser sensor and a video sensor, wherein one of the sensors is selected according to the measuring task. EP-A-1 389 263 proposes replacing one of these sensors with a computer-tomograph.

Whenever x-ray sensor systems are used, comprehensive safety measures for shielding against x-ray radiation are necessary for compliance with radiation protection regulations. It must be ensured that the radiation exposure does not exceed the threshold prescribed for the measuring apparatus. A commonly known approach to meeting these requirements is to arrange around the measuring apparatus, hence independently thereof a radiation protection housing that is made of lead or lead-coated composite material. The radiation protection housing has the exclusive task of absorbing the x-ray radiation emitted by the computer-tomograph. The additional housing adds to the volume of the total measuring apparatus. This in turn results in an undesirable increase in weight as well as high cost.

A further disadvantage of computer-tomographs of the prior art is that the measuring speed remains below that which coordinate measuring technology can achieve with optical sensors. Another disadvantage is the fact that the computer-tomograph is fixedly secured to the basic assembly of the coordinate measuring device, which in turn limits the range of measuring applications that can be performed.

US-A-2003/0043964 discloses an inspection system for airplane fuselages that comprises an x-ray source that works from a crane and is positioned inside the fuselage as well as a sensor that works from a crane and is positioned outside the fuselage. Triangulation is employed to determine the position of the sensor.

A measuring device described in DE-A-100 01 239 features a position detector, along with a non-optical measuring system such as an AFM (atomic force microscope), which are fixedly connected to one another by a bearing element.

A multi-sensor measuring head disclosed in DE-A-44 45 331 comprises a vertical axis on which a plurality of sensors can be mounted.

In a coordinate measuring device described in EP-A-0 504 609, articulated milling heads are employed in addition to measuring heads.

An x-ray testing apparatus described in U.S. Pat. No. 5,038,378 provides the possibility of adjusting x-ray detectors independently of each other along three axes.

The goal of the present invention is to further develop a method and a coordinate measuring device for measuring an object with at least one x-ray sensor system as its first sensor system, as well as a second sensor system in the form of a tactile and/or an optical sensor system, so that objects of measurement of greater size can be measured without difficulty. Additionally, an increased degree of measurement accuracy compared to that of the prior art should be achieved. Furthermore, it should be possible to perform a geometric calibration of the x-ray sensor system (computer-tomograph) by following a simple set of instructions. The apparatus should be of compact construction, while, at the same time, sufficient shielding against x-rays should be ensured. High measurement densities and high measuring speeds should be achievable through simple means. Furthermore, improved resolution and a reduction of signal-to-noise ratio should be facilitated. It should be possible to perform sufficiently precise measurement of objects that yield low contrast when subjected to x-rays.

To solve one aspect of the invention, a coordinate measurement device is proposed for measuring an object with an x-ray sensor system, the first part of the sensor system comprising an x-ray source and at least one x-ray sensor that measures the x-ray radiation, as well as a second sensor system, such as a tactile and/or optical sensor system that can be positioned relative to the object along the x-, y- and/or z-axes of the coordinate measuring device. The proposed system is distinguished by the fact that the x-ray sensor system corresponding to the second sensor system can be positioned within the coordinate measuring device. In other words, the x-ray sensor system equivalent to the second sensor system is arranged inside the coordinate measuring device, while, in principle, the positioning of x-ray sensor systems and the analyzing of their data can be managed by the same components or hardware and software, which, in principle, can also be employed for any additional sensors. The second sensor system can in turn comprise more than one sensor.

The invention therefore proposes, among other things, that the x-ray sensor system (computer-tomograph) is not fixedly attached to the coordinate measuring device, but rather that it is fully integrated into the coordinate measuring device as a sensor system. The senders and receivers of the computer-tomograph are also arranged in the coordinate measuring device in a configuration that is conventional in transillumination and image-processing sensor technology. X-ray receivers and image-processing sensor or mechanical probes can be movably arranged on a common mechanical axis. It is equally possible to employ a separate axis for each sensor. The respective radiation sources for visible light radiation and x-rays are arranged opposite their respective sensors.

By means of the inventive setup, it is possible to sequentially capture multiple sections of the object of measurement through the known process of tomography (rotating the part and taking multiple x-ray images). The entire collection of assembled x-ray images can then be used to generate a 3D-construction. The size of the objects that can be measured is thereby not limited to the visual field of the tomograph.

According to the invention, multiple tomographic images are arranged in sequence using the coordinate measuring device or the coordinate system of the measuring device.

It is also possible to measure those features of an object of measurement that require more precise measurement in a traditional manner by using the sensors of the multi-sensor-coordinate measuring device (e.g. for tactile-optical measurement). X-ray sensors and image-processing sensors and tactile sensors perform measurements using a common coordinate system, as is conventional practice for multi-sensor-coordinate measuring devices. This allows the measurement results to be related directly to one another.

With the given setup, it is now possible to perform the calibration of the measurements with the x-ray sensor system directly on the object of measurement itself using the principle of tomography. Marked points on the measuring object are measured with the tactile or optical sensor system of the coordinate measuring device at a known level of precision. These points are factored into the analysis of the computation of the 3D-reconstruction of the computer-tomograph to facilitate the geometric calibration of this reconstruction process.

To ensure sufficient shielding against x-ray radiation when a compact setup is employed, the invention proposes, among other things, that the shielding or at least an area thereof be designed as a functional component of the required measurement technology setup of the coordinate measuring device. This component can, for example, be the housing of the mechanical axis or the axis itself, base plates, supports etc., provided this does not have a negative impact on the invention. In other words, the shielding necessary for radiation protection is taken over completely or in part by functional components of the measurement technology setup of the coordinate measuring device.

In particular, it is possible that the base plate and at least the rear wall of the housing of the coordinate measuring system are made to a certain thickness or manufactured of a certain material so that they can provide the required shielding. The base plate or a side wall can also be designed in this way. In particular, it is proposed that the components relevant for the shielding be composed of hard stone such as granite. It is also possible to use other materials, particularly artificial stone, which, if necessary, are treated with an appropriate radiation-absorbing material.

In a further development of the invention, the shielding or, as the case may be, the components of the coordinate measuring device such as walls that form the shielding, can be the mounting site for functional components of the coordinate measuring device. Accordingly, shield-forming components can be used at the same time for the assembly of functional components of the coordinate measuring device, in particular the computer tomograph to be employed, where the functional components can be mechanical axes or traveling axes and/or sensors and/or radiation or light sources.

To ensure sufficient shielding, the components used for the shielding can be of thickness greater than that required for measurement technology or static use.

According to one inventive proposal, several sensors are assigned to the x-ray source, the differing irradiation angles of the sensors crossing in the object, while, particularly for measuring an object, n-sensors simultaneously struck by x-rays are assigned to the x-ray source, the x-ray source can be adjusted between consecutively performed measurements relative to the object at a base angle $\alpha$ and sensors arranged one after the other can each be rotated in relation to the neighboring sensor by an angle $\alpha/n$.

The inventive arrangement comprises n detectors for the x-rays, which are arranged so that with each detector or sensor an x-ray image is taken at a different irradiation angle, whereby a decrease of the required angular position for generating a tomogram is necessary.

According to the invention, the x-ray sensors are adjusted in relation to one another by an angular difference that is calculated as follows. A base angle is used that is a whole-number multiple of the angular step used between the radiation source and the sensor on one hand and the object to be measured on the other hand, where the object is on a rotating table, particularly one that can be rotated in relation to the x-rays sensor system. The angle of the second sensor is increased by a value of 1/(number of sensors), while the angle of the third sensor is increased by a value of 2/(number of sensors). Accordingly, the $n^{th}$ sensor is increased by $(n-1)/$(number of sensors). For a single revolution, it is thus possible to ascertain the u-times number of angular positions, where u=the product of n (the number of sensors) and m (the number of times the object is positioned in relation to the x-ray sensor system).

According to the invention, the x-ray sensors are adjusted in relation to one another by a whole number multiple of the angular step of the rotating table, while the irradiation time can be decreased for each angular position. Regardless of this, the plurality of x-rays is captured by the plurality of sensors, thereby reducing the signal-to-noise ratio.

An inventive embodiment provides that in the process of image taking or, as the case may be, image transmission or image evaluation, multiple pixel elements of the sensors are combined into one pixel and the original resolution in the volume image, which is computed from the images with correspondingly reduced pixel count, is achieved or exceeded through mathematical interpolation.

After 2D-images are taken by means of tomography, the existing 2D-image can be converted into a lower resolution image with less pixel information through, for example, averaging of neighboring pixels. Using these lower resolution images, 3D-reconstruction is then performed to generate a three-dimensional voxel image from the different 2D x-ray images. After this voxel image is defined, the voxel-image is computed back into an image of the original resolution through interpolation between multiple voxels. It is even possible to calculate additional voxels through further application of the same approach using certain algorithms, thereby achieving a higher resolution voxel image.

Also inventive is the idea that the object is continuously rotated during measurement, while the x-ray source is only briefly opened multiple times with the aid of a mechanical or electronic shutter, for example, or other measures that produce the same effect such as high-frequency modulation to prevent motion artifacts. Regardless of this, shortened measuring time is achieved in this manner.

Another embodiment also provides for multiple tomograms to be generated from the object through the use of various spectral ranges of the x-rays. The spectral range of the x-rays is determined by the cathode voltage of the x-ray generator. Typically—but purely as an example—the object of measurement could be tomographically imaged with a cathode voltage of 50 kV and 90 kV and 130 kV. Then, on the basis of the differences in measurement results at the different cathode voltages, specifically x-ray color or x-ray frequency, the magnitude of systematic measurement deviations, such as, for example artifacts, can be ascertained and then corrected.

Multiple tomograms can also be taken of an object, while the angle between rotation axis of the rotating table holding the object and x-ray source and attached sensors can be varied among various angle settings with the aid of mechanical rotational swivel axes or through the use of multiple detectors, while the sensors extend in particular along a straight line running parallel to the rotation axis of the rotating table.

To increase the resolution of the tomogram, multiple images can be taken, while, in the intervals between images, the sensor or the object is shifted by a distance that is smaller than an edge length of a sensitive element of the sensor.

The invention also proposes that the object be penetrated by parallel running x-rays. The x-rays are parallelized with the aid of suitable devices.

Additionally or alternatively, it is also possible, with the aid of translatory relative movements between the object to be measured and the x-ray source/sensor, to image an area that is larger than the surface area of the sensor.

In order to image workpieces that exhibit only low contrast to x-rays, the invention proposes that the object be enveloped by a material that features higher absorption than the object itself. In the case of an object of measurement made of a material with low mass number, such as lithium, the contrast of the tomographically obtained 2D-x-ray images can be improved by coating the object of measurement with a heavier material. Images of sufficiently high contrast are thus obtained from the negative form of the object of measurement and in turn facilitate a representation of the object of measurement.

To achieve optimal measurement, different kinds of sensors can be used in the measurement process. It is proposed that in addition to the x-ray source and the sensors attached thereto, additional sensors for the measurement of the object such as mechanical probes, laser probes and image-processing sensors are provided in the setup and, if necessary, are arranged on separate traveling axes.

The rotation axis facilitating the rotation of an object necessary for taking a tomogram can be arranged on a traveling axis, whereby the measurement area is expanded in the direction of the rotation axis. In other words, the object can be adjusted in the direction of the rotation axis.

An inventive proposal for calibrating the x-ray sensor system in the coordinate measuring device provides that marked points of the object to be measured are measured with a tactile and/or optical sensor system to ascertain geometrical features such as diameter or distance, which are then used for the calibration of the x-ray sensor system after the same geometrical features have been ascertained with the x-ray sensor system.

The measurement results obtained through tactile and/or optic sensor systems for marked points such as peripheral areas of the measurement volume can thus be implemented in the correction of the measurement point cloud generated from the 3D-voxel-data by means of the thresholding.

The thresholding operation employed following tomography generates 3D-point clouds, which can be represented in ASCI-format or STL-format. This point cloud is adjusted between the tactilely or optically ascertained measurement point in such a way that the deviations between tactile and/or optical measurement and the tomographic measurement are kept to a minimum. An interpolation is performed between the tactile and/or optical measurement points to determine the deviation.

When the voxel is calculated by means of 3D-reconstruction, the positions of the voxel, which are located on the material margins (edges of the measurement volume) of the object imaged through tomography, are adjusted by the correction value ascertained through tactile or optical counter measurement. Voxel positions between control points are then corrected through interpolation between the measured correction positions. An irregular voxel raster in three-dimensional space is hereby generated, with the voxel locations corresponding more to the actual object geometry than to the original voxel image. This voxel-image is then advantageously resampled in a regular raster. This can be achieved by prescribing a target raster for the voxel image and by generating a new voxel amplitude from the voxel surrounding voxel-amplitudes through interpolation for each point of the target raster.

To achieve a high degree of measurement certainty and to facilitate a geometrical calibration of the x-ray sensor system (computer-tomograph) in a simple manner, the invention proposes that the positions for x-ray source and x-ray detector be stored with the appropriate calibration data for specific magnification and measurement range devices following a single calibration and that they can be called up for subsequent measurements as desired through software without any further recalibration.

In other words, the invention provides that all adjustment parameters necessary for tomography at a certain magnification or a certain measurement range—this includes the position of the various axes of the tomography or coordinate measuring device—as well as the magnification values and other calibration data assigned to these positions including correction values for positioning the axis in relation to the position measurement delivered by the connected displacement measurement systems are recorded in a single calibration procedure of the coordinate measuring device and stored. In normal operation of the coordinate measuring device, these stored values are then called up by the user at the touch of a button or by a CNC-program, the machine is moved into the appropriate positions and the appropriate calibration data is then used in the subsequent measuring process.

It is provided in particular that previously calibrated magnification and measurement range settings are automatically called up by the measurement program of the coordinate measuring device and the corresponding hardware components of the device are positioned.

It is also possible to have the x-ray source and the x-ray detector synchronously driven to change only the magnification and/or measurement range or to move the x-ray source and the x-ray detector independently of one another to change the magnification and/or measurement range.

It is also possible to have all settings necessary for radiographic measurement (tomography) calibrated and stored in advance, so that for each radiographic measurement procedure, such as a tomography procedure, calibration procedures are no longer necessary.

Adjustment of the rotation center can be realized through a calibration procedure and/or a corresponding correction of the rotation center drift in the software.

In another embodiment, the magnification for the tomography and/or the position of the rotation center in relation to the x-ray source and x-ray detector is determined using a standard that consists of at least two spheres. In this particular case, the standard consists of four spheres.

A method for determining the position of the rotation center in a coordinate measuring device is distinguished in particular by the following steps:

A four-sphere standard consisting of four spheres arranged at the corners of a rectangle such as a square, wherein the spacing of the spheres in relation to one another is known or calibrated, is positioned on the rotation axis, the four-sphere standard is rotated so that the mounted plane is parallel to the detector, Measurement of the four-sphere position in the measuring field of the detector, Calculation of the average magnification M1 from the four measured sphere distances, the nominal sphere distances and the nominal pixel size of the detector, Rotation of the rotation axis by 180°, Measurement of the four sphere positions in the image, Calculation of the average magnification M2 from the four measured sphere distances, the nominal sphere distances and the nominal pixel size of the detector.

The Y-position of the rotation center is calculated from the four sphere positions prior to and following the rotation using the following formula: $Pdyn=(Pkyn1*M2+Pkyn2*M1)/(M1+M2)$ with Pdyn being the Y-position of the rotation axis on the detector for sphere n, Pdy1 being the Y-position of the sphere n at a rotation angle 0°, Pkyn 2 being the Y-position of the sphere n at a rotation angle 180°, M1 being the average magnification at a rotation angle 0° and M2 being the average magnification at a rotation angle 180°.

It is also possible to measure an object using a coordinate measuring device that features other sensors in addition to x-ray sensor systems (computer-tomographs), allowing the measurements to be performed by means of a tactile or optical sensor system, with tactile-optical measurements being mentioned in particular. It is thus possible to have the measurement point cloud of the object of measurement measured with an x-ray sensor system or tomography or the triangulated surface element calculated from this data corrected through tactilely or optically obtained measurement points, while values can be interpolated between the tactilely or optically measured correction points.

Values can also be interpolated between correction points obtained with tactile and/or optical sensor systems while factoring in the functional course of the point cloud obtained through an x-ray measurement procedure such as tomography and/or while taking into consideration the nominal CAD-model.

For the measurement of repetitive parts, another proposal provides that a sample part of the type of object of measurement is scanned using x-rays (tomographically) as well as tactilely and/or optically, a correction network for the correction of the tomographic measurement values is calculated from the difference of both measurements and the tomographic measurements are corrected with the correction values obtained one time.

This approach can be understood as involving a first measurement procedure, in which many measurement points of a typical representative of the object of measurement are tomographically and tactilely or optically measured using x-rays. In this case, a great many measurement points are used, also in tactile and/or optical measuring, to achieve a sufficiently dense correction network. From this data, corresponding correction values, which result from the comparison of the tactile and/or optical measurement values with the tomographic measurement values, are then determined for each surface position of the object that undergoes tomography. When additional parts later undergo tomography, these correction values are directly applied. It is not necessary to perform another tactile or optical counter measurement.

For the measurement of repetitive parts, it is accordingly provided that a calibrated portion of an object of measurement undergoes tomography, that a correction network for the correction of tomographic measurement values is calculated from the measurement deviation occurring during measurement, and the tomographic measurements are adjusted with the previously calibrated correction values.

When repetitive parts are measured, individual correction points, optically and/or tactilely measured, can also be factored in.

For correction, the tactile and/or optical measurement points can be graphically plotted by an operator on the point cloud generated by tomography and can then be measured automatically by the coordinate measuring device.

In another configuration, the tactile and/or optical measurement points for correction are graphically plotted by an operator on the CAD-model of the part to be measured and are then automatically measured by the coordinate measuring device. The tactile and/or optical measurement points for correction, evenly or nearly evenly distributed by an automatic algorithm on the surface of the CAD-model of the part to be measured, are automatically measured by the coordinate measuring device. The tactile and/or optical measurement points for correction can be graphically plotted on the CAD-model by an operator and, after the CAD-model has been loaded, can be automatically measured by the coordinate measuring device.

The invention also teaches that in tomography procedures, a calibration body, in particular an arrangement of spheres, is in principle imaged through tomography, thereby allowing the relative position of the rotation axis in relation to the coordinate measuring device and/or to the x-ray source and/or to the x-ray sensor to be determined and then mathematically corrected. Using this means, the position of the calibration bodies on the rotation axis can be ascertained with optical and/or tactile sensors and used for correction of the position of the rotation axis.

It is also provided, in particular, that the calibration body, as well as the minimum of two calibration spheres in the holding device, which is the rotating table of the object to be measured, are incorporated into a material with low absorption of x-rays. The object of measurement can thus be positioned on the rotating table through the detection of the calibration body, since the position of the center of rotation, and hence the rotation axis of the rotating table, can be ascertained using the calibration body.

According to the invention, the spatial location of the rotation axis in relation to the x-ray source and x-ray detector can be ascertained with the x-ray sensor system and/or with the tactile sensor system and/or with the optical sensor system, and this deviation in position can be mathematically corrected when objects of measurement undergo tomography.

In particular, the position of the rotation axis deviating from the nominal position can be corrected through rotation and/or translation and/or distortion of the 2D-single images.

Furthermore, the position of the rotation axis deviating from the nominal position can be factored into the reconstruction algorithm.

Another proposal of the invention provides that the position of the object of measurement on the rotating table, and thus in the machine coordinate system, is ascertained using tactile and/or optical sensors and/or tomography and then measured in 2D-x-ray mode at calibrated position of the x-ray sensor on the basis of mass through methods of image processing.

These measures illustrate an additional operational principle of the inventive coordinate measuring device in which an x-ray sensor system is integrated. The possibility of measuring in 2D-x-ray images is thus achieved. Conventionally this is not possible, as the actual magnification on the object of measurement is not known. This is the case because the position of the object of measurement in the x-rays path is not known, and position, according to Thale's theorem, essentially determines magnification. If the position of the object of measurement in the coordinate measurement device is precisely determined with an optical and/or tactile sensor system, the magnification of the currently irradiated object of measurement is known on the basis of this position and the use of an x-ray sensor system for two-dimensional measurement with methods of image-processing is thereby possible.

The x-ray detector can be automatically controlled via the device-software, so that the detector is positioned in the radiation cone of the x-ray source during the actual tomography procedure and, at other times, is brought into parked position outside the radiation cone.

Through these measures, the amount of radiation to which the x-ray sensor is exposed is minimized, thereby extending the life of this component.

The invention also provides for the image-processing sensor system and the x-ray sensor system of a multi-sensor coordinate measuring device to be outfitted with the same image-processing-hardware and the same image-processing-software or parts thereof The image processing methods known from image-processing sensor technology can also be used for an x-ray sensor system.

The invention also provides that prior to reconstruction, the 2D x-ray images undergo distortion correction and/or bright signal correction and/or dark signal correction and/or mathematical translation and/or mathematical rotation and/or a resampling process and/or linearity characteristic line correction and/or image processing filtering.

Preferred embodiments of the invention are described in both the claims and subclaims.

Additional details, advantages and features of the invention can be found not only in the claims and the features detailed therein, individually and/or in combination, but also from the following description of the preferred embodiment illustrated in the drawings.

Shown are:

FIG. 1 a schematic diagram of a multi-sensor coordinate measuring device

Figure 2:
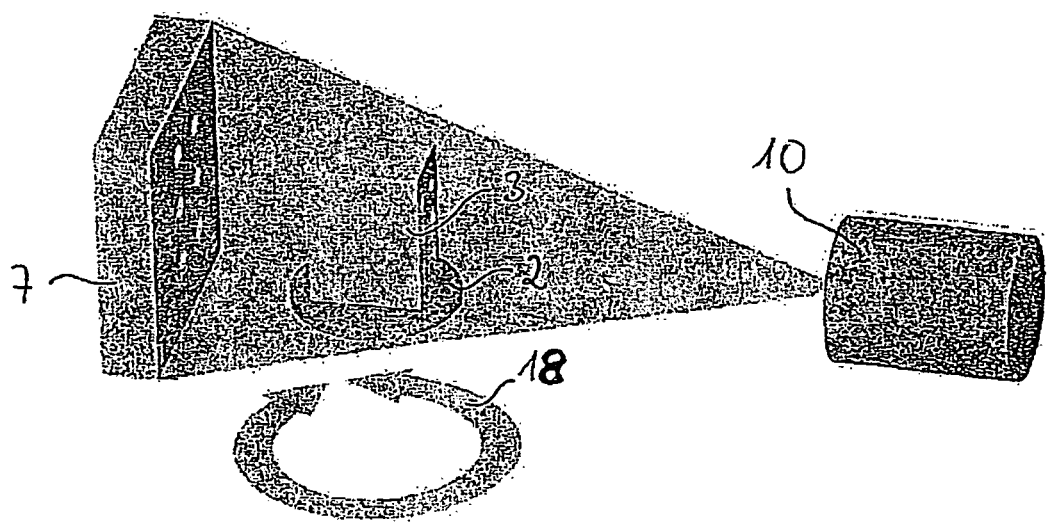

FIG. 2 a functional diagram of a 3D-computer tomograph

Figure 3:
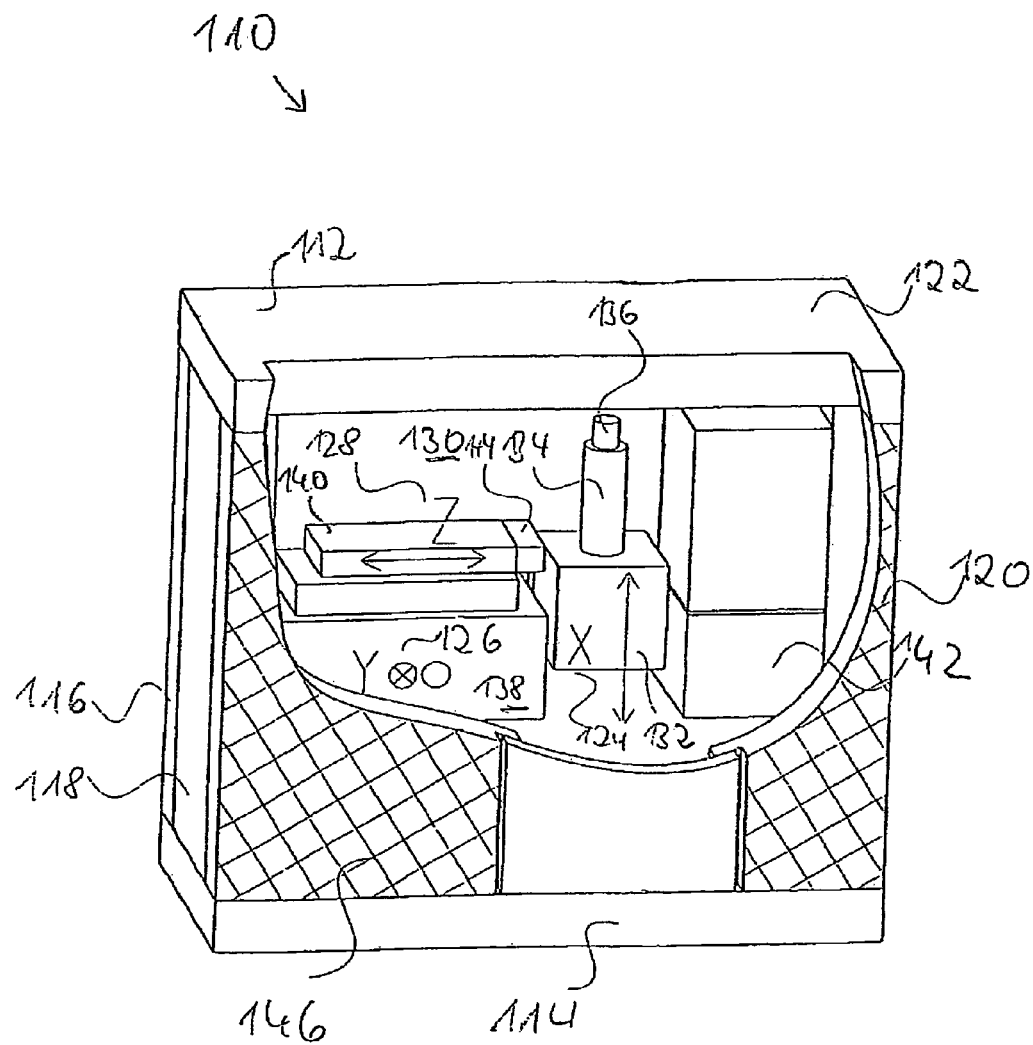

FIG. 3 an additional schematic diagram of a coordinate measuring device

Figure 5:
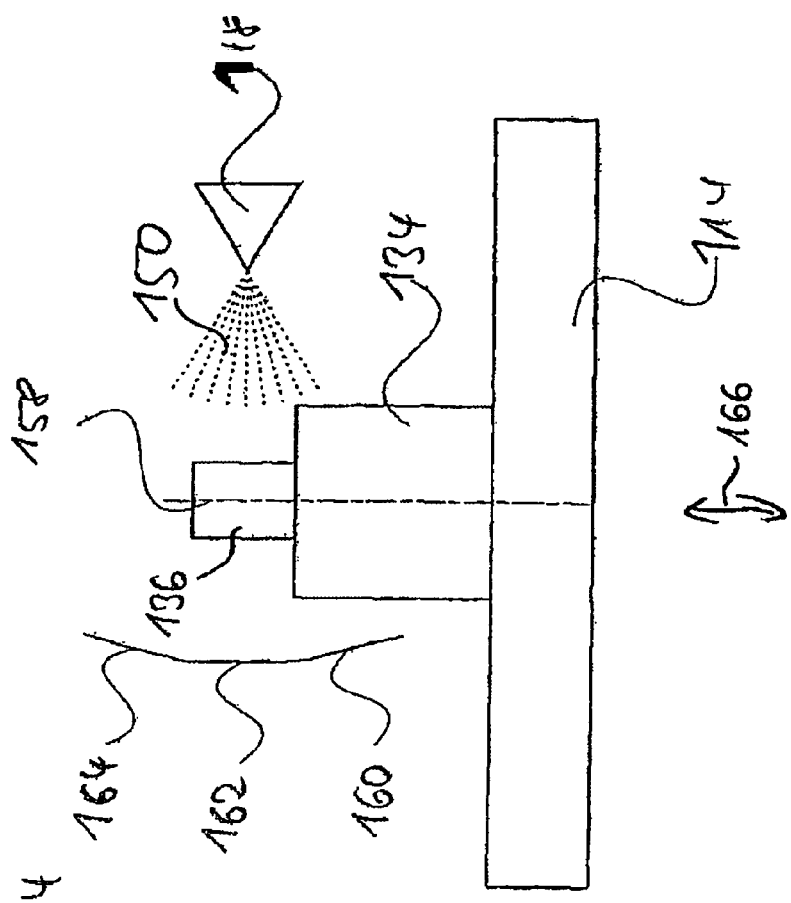
Figure 4:
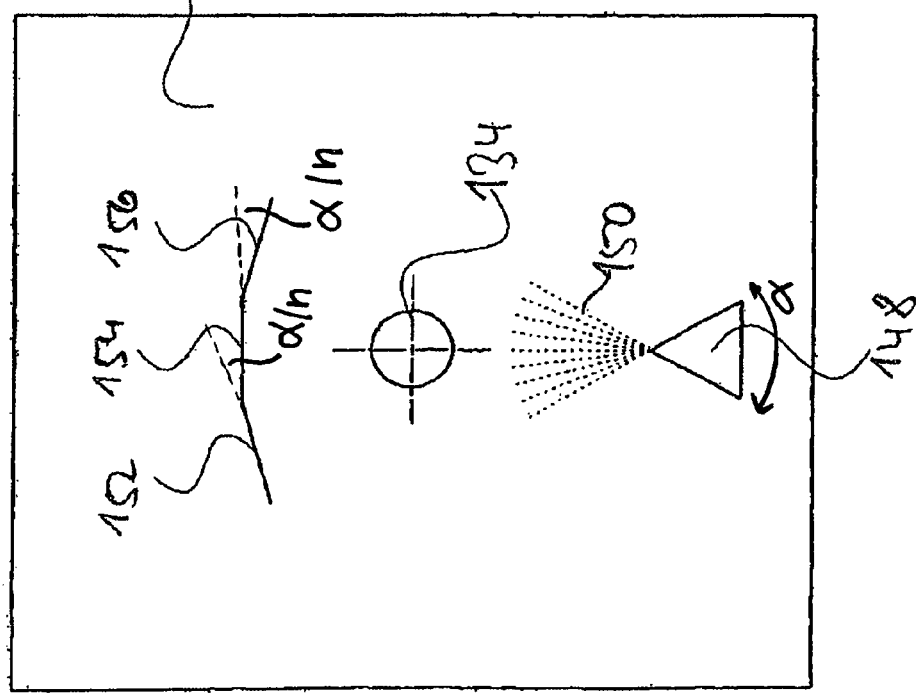
Figure 6:
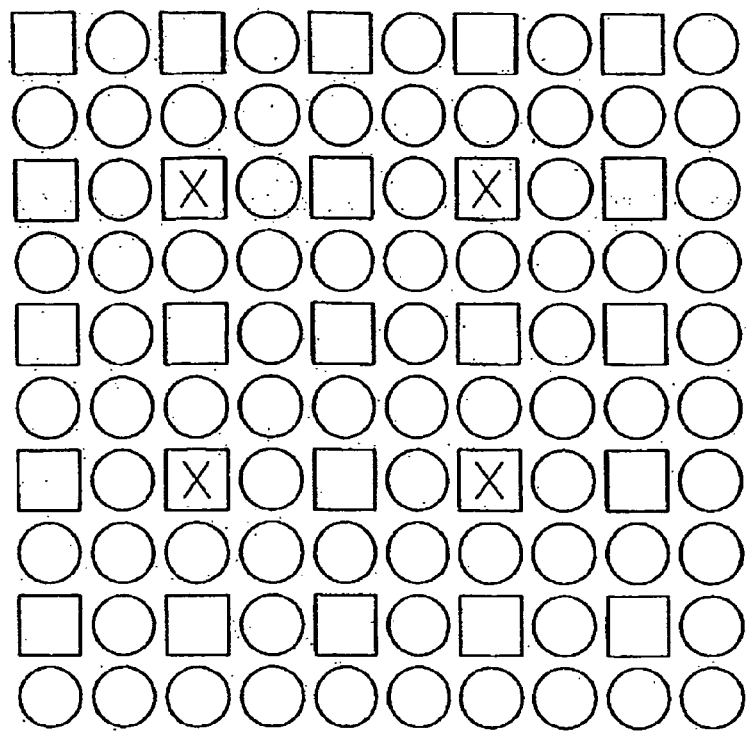
Figure 7:
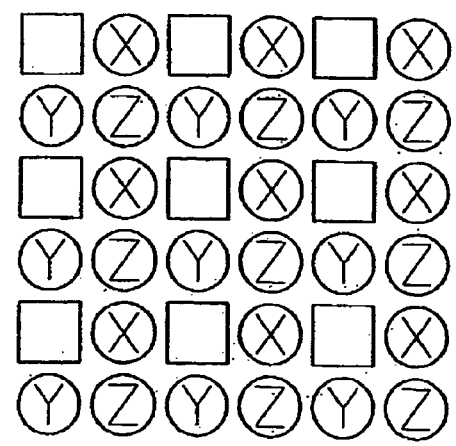
Figure 8:
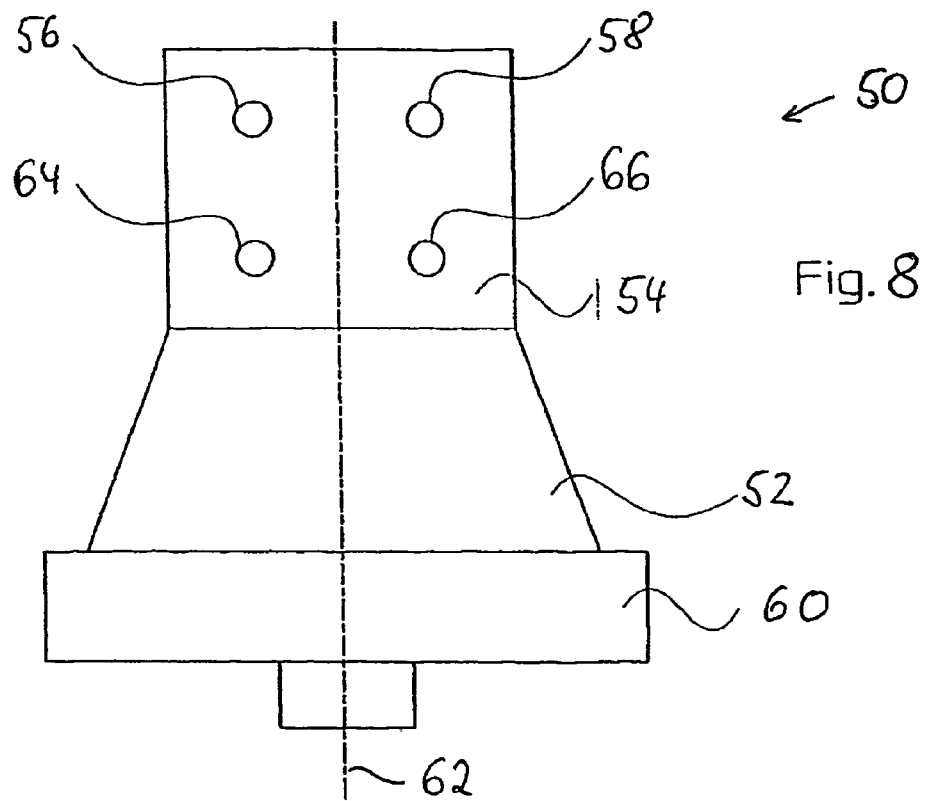
Figure 9:
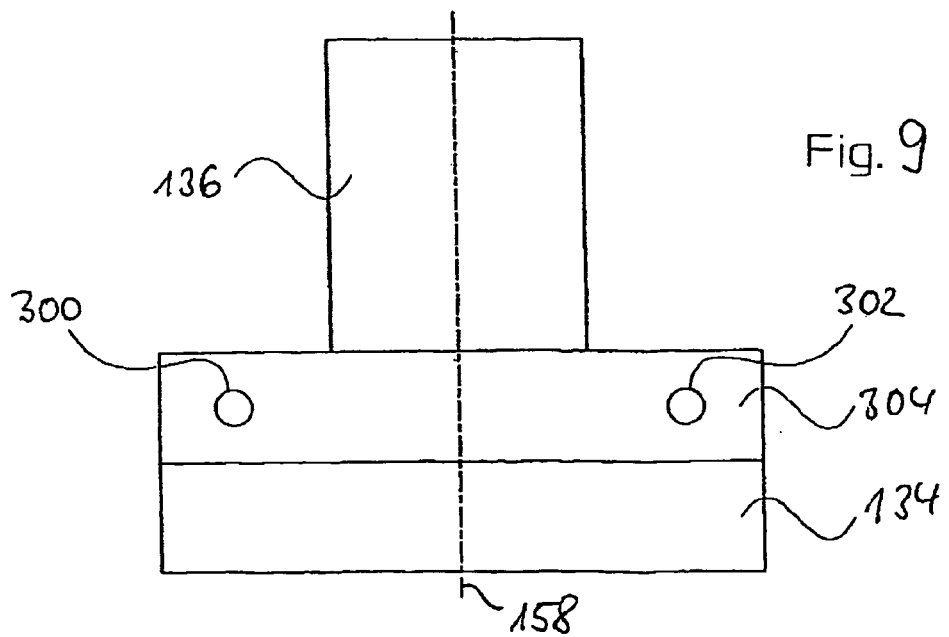
Figure 10:
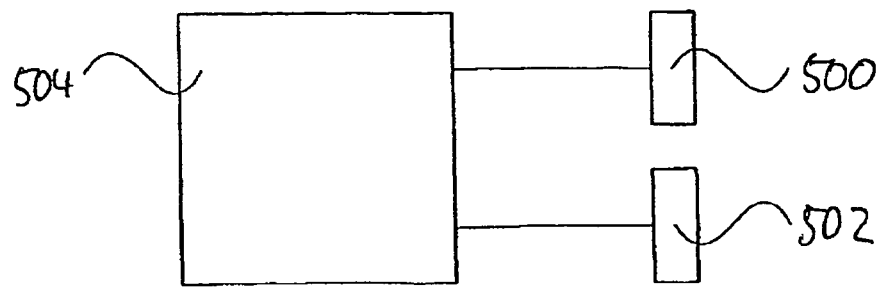
Figure 11:
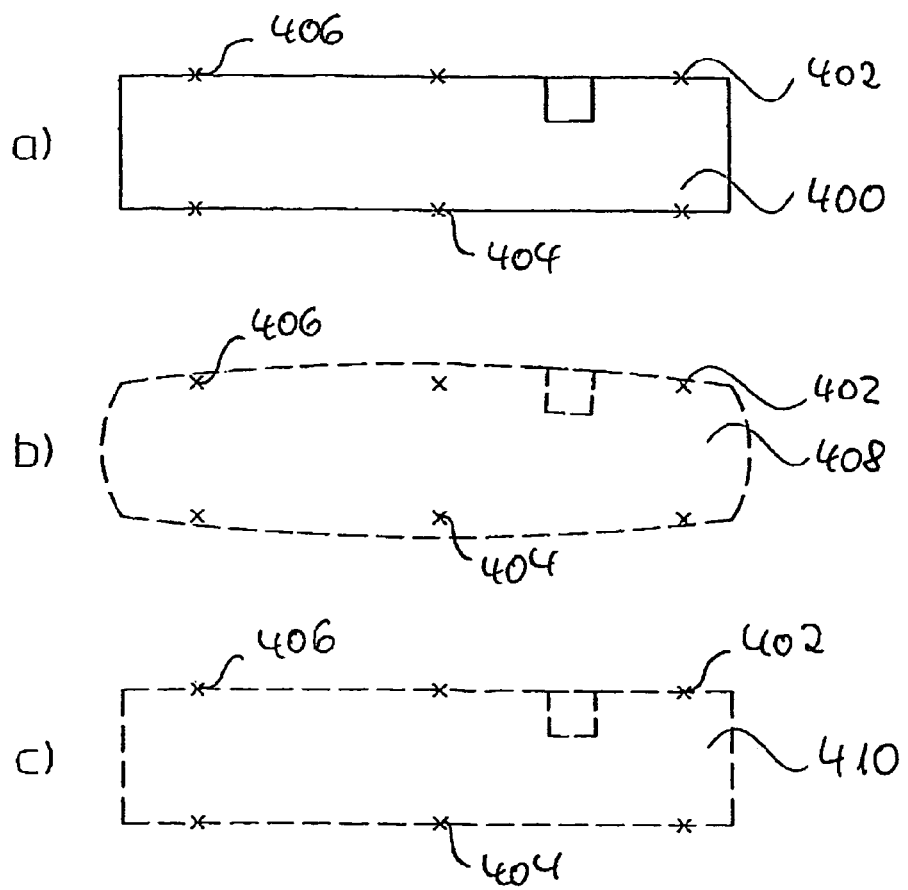

FIG. 4 a schematic diagram of a first arrangement of x-ray source and assigned sensors FIG. 5 a schematic diagram of a second arrangement of x-ray source and assigned sensors FIG. 6 a schematic diagram for image evaluation FIG. 7 a schematic diagram for illustrating a process for increasing the resolution of a tomogram FIG. 8 a schematic diagram of a calibration body FIG. 9 a schematic diagram of a rotating table with a calibration body FIG. 10 a block diagram and FIG. 11 a conceptual diagram to illustrate a correction process.

FIG. 1 is a schematic diagram of a coordinate measuring device for the combined use of an x-ray sensor system and an optical and tactile sensor system, even if the invention is essentially suited for features of a coordinate measuring device that comprises no additional sensor system beyond the computer-tomograph.

Arranged on an axis 18 running parallel to the X-axis is a rotating table 2. Present thereon is an object of measurement 3, which can thus be rotated on a rotation axis 18 and displaced by the axis 18 in the direction X (double arrow). Arranged on a slide 4 running parallel to the Y-axis are two axes 5, 6 running parallel to the Z-axis. Located on the mechanical axis 5 is a sensor 7 for x-rays and an image-processing sensor 8. Additionally located on the mechanical axis 6 is a tactile sensor 9. Arranged opposite the x-ray sensor 7 is an x-ray source 10, which can be mounted either movably in the direction of Y or fixedly as desired. Opposite the image-processing sensor system 8 is a transmitted light source 11. The mechanical axes and slide, which run along the X-, Y- and Z-axes of the coordinate measuring device, are designed so that sensors installed in or on the coordinate measuring device can each cover the entire measurement range on the rotating table 2.

The integration of computed-tomography (CT) into a multi-sensor coordinate measuring device creates entirely new possibilities. A quick, nondestructive complete measurement with tomography is combined with high-precision measurements of functional dimensions with tactile or optical sensor system. The invention provides that the x-ray sensor system (sensor, radiation source) corresponding to the second sensor system (e.g. image-processing sensor, transmitted light beam source or incident light beam source or tactile sensor, if necessary with attached image-processing sensor) can be positioned in the coordinate measuring device so that the x-ray sensor system is arranged equally with the second sensor system. The x-ray sensor system can be arranged with at least the tactile sensor system and/or the optical sensor system on a common mechanical axis or on a separate mechanic axis that functions analogously to the mechanical axes for the tactile and/or optical sensor system.

The functional principle of 3D-computed tomography is illustrated using FIG. 2. The reference numbers for the elements shown in FIG. 1 are retained.

The workpiece 3 is disposed on a rotating table 2 and transilluminated with x-rays. The sensor 7, shown here for example in the form of a surface detector, converts the x-ray image into a digital 2D-image for further processing. The object 3 is turned 360° and x-ray images are taken in multiple rotational positions. The 2D-images are then used for a 3D-reconstruction of measurement points that describes the entire workpiece geometry to be measured. Through the integration of one or more of the additional sensors 8, 9 the range of applications of the computer-tomograph can be expanded. The image-processing sensor 8 allows the fully automatic measurement of complicated, extremely low-contrast workpieces in transmitted light and incident light. Tactile sensing systems facilitate high-precision measurements of optically inaccessible features.

It is also possible to adjust the sensor 7 and the x-ray source 10 synchronously to the object, that is, with their distance to one another remaining the same. This allows an adaptation of measurement range, which, if necessary, can be automatic. Alternatively, the object 3 can be shifted in relation to the sensor 7 to facilitate an adaptation to the workpiece size and the precision requirements. If the object 3 is shifted toward the sensor 7, lower magnification is achieved, whereas if the object 3 is shifted toward the x-ray source 10, a greater magnification can be achieved. If a stationary x-ray source 10 is used, the sensor can also be shifted toward the object 3.

The invention offers the following particular advantages:
Complete detection of all fixed and free form geometries of a workpiece in a single measurement procedure,
Measuring interior geometries and inaccessible features (e.g. obscured edges, undercuts),
High precision measurement of functional dimensions with tactile or optical sensor system,
Recirculation of tomographic measurement results through multisensor technology,
Combine measuring with tomography and other sensors in a measurement cycle
2D- and 3D-measurements of form, dimensions and position,
Comprehensive functions for 2D-measurement in x-ray images,
3D-target-actual comparison as 3D-deviation display in comparison with 3D-CAD-model,
Generation of 3D-CAD-data from acquired CT-data.

FIG. 6 illustrates an additional method characterizing the invention that facilitates a compression of data without sacrificing resolution. In fact, the corresponding teachings even make it possible to surpass the original resolution. This is explained using a 2D-image.

In FIG. 6 the squares represent the pixels of a 2D-image. The present 2D-image is converted into a lower resolution image with less pixel information (pixels illustrated as crosses) through, for example, averaging the neighboring pixels. From corresponding 2D x-ray images of lower resolution a 3D-reconstruction for computing the three-dimensional image is then performed. After this voxel image has been defined, the voxel-image, which in the 2D-illustration shown in FIG. 6 is also simulated through crosses, is then computed back into an image of the original resolution through interpolation between multiple voxel images, so that an image with squares—also shown as a 2D-illustration—is yielded. Using the same approach, it is also possible to compute additional voxels to achieve a higher resolution of the voxel image. This is symbolized with circles.

In this way, computation can be performed faster, because a lower resolution can be used at first without requiring resolution to be sacrificed in the end. In fact, resolution can even be surpassed.

Using FIG. 7 for reference, a further inventive method is examined that allows the resolution in the tomogram to be increased. To achieve this end, multiple shots are taken, while during the intervals between shots, the sensor is shifted in relation to the object or the object is shifted in relation to the sensor by a distance that is smaller than the edge length of a sensitive element of the sensor. In FIG. 7 the resolution of the x-ray detector (sensor) employed is illustrated by pixels drawn as squares. During the process of tomography, for each rotational position, an image is taken in the position of the x-ray detector represented as a square along with an image taken in the position of the x-ray detector represented as a circle with an X, along with one in the position of the x-ray detector represented as a circle with a Y, along with one in the position of the x-ray detector represented as a circle with a Z. All images are assembled to form an image and are recognized as single entity during the tomography reconstruction process. A higher resolution is thereby achieved than is physically provided by the detector.

To determine the magnification for the tomography and/or the rotation center of the rotating table 2 in FIG. 1 in relation to the x-ray source 10 or the sensor 7, a standard can be used, which in the embodiment illustrated in FIG. 8, is labeled 50. In the schematic diagram, a bearing element 54 made of a material with low x-ray absorption extends from a stand 52. Arranged in the bearing element 54 are at least two spheres 56, 58 of a material with high x-ray absorption, such as steel. The standard 50 is then arranged on a tomograph rotating table 60, which corresponds to the rotating table 2 from FIG. 1. The rotating table 60 can be rotated on an axis 62, which overlaps the X-axis of the coordinate measuring device. The measurement procedure for determining the position of the rotation axis 62 of the tomograph within the coordinate measuring device is now determined through measuring the position of the spheres 56, 68 relative to the x-ray sensor in various rotational positions of the sphere standard 50.

If the magnification level is to be ascertained, then it is necessary to take measurements at two different distances from the sensor 7.

To facilitate a high degree of precision, the standard 50 can feature two additional spheres 64, 66.

Below it is described how the distance between the x-ray source 10 and the sensor 7 is determined by means of a standard, which in the embodiment consists of a four-sphere standard comprising four spheres arranged at the corners of a square.

The distances among the spheres are known (calibrated).
The four-sphere standard is arranged on the rotation axis.
The four-sphere standard is rotated so that the mounted plane is parallel to the detector.
Measurement of the four sphere positions in the image at position Z1
Calculation of the average magnification M1 from the four measured distances among the spheres,
the nominal distances among the spheres and the nominal pixel size of the detector
Driving the rotation axis in the direction of the source (or source and detector perpendicular to the rotation axis)
Measurement of the four sphere positions in the image at position Z2
Calculation of the average magnification M2 from the four measured distances among the spheres,
the nominal distances among the spheres and the nominal pixel size of the detector
Calculation of the distance between source and detector using the following equation:

$$AQD = dZ * M1 * M2 / (M2 - M2)$$

where:
AQD: Distance source-detector
M1: Magnification at position Z1
M2: Magnification at position Z2
dZ: Distance between position Z1 and Z2
Calculation of the distance from source to Z1 using the following equation $$D1 = dZ * M2 / (M1 - M2)$$

Calculation of the distance from source to Z2 using the following equation $$D2=D1+dZ=dZ*M1/(M1+M2)$$

Calculation of the position of the cone axis on the detector using the following equation $$Pd=(Pkn1*D1-Pkn2*D2)/dZ$$

where:
Pd: Deviation vector of the cone axis-position from the center of the detector
Pkn1: Position vector of the sphere n on the detector at position Z1
Pkn2: Position vector of the sphere n on the detector at position Z2
Calculation of the average deviation vector from the four deviation vectors for each sphere position A method for determining the Y-position of the rotation axis center, also while using a four-sphere standard comprising four spheres arranged at the corners of a square, proceeds as follows:

The distances among the spheres are known (calibrated).
The four-sphere standard is arranged on the rotation axis.
The four-sphere standard is rotated so that the clamped plane is parallel to the detector.
Measurement of the four sphere positions in the image
Calculation of the average magnification M1 from the four measured distances among the spheres,
the nominal distances among the spheres and the nominal pixel size of the detector
Rotating the rotation axis by 180°
Measurement of the four sphere positions in the image
Calculation of the average magnification M2 from the four measured distances among the spheres,
the nominal distances among the spheres and the nominal pixel size of the detector
Calculation of the Y position of the center of rotation from the four sphere positions prior to and following the rotation using the following equation:

$$Pdyn=(Pkyn1*M2+Pkyn2*M1)/(M1*M2)$$

where:
Pdyn: Y position of the rotation axis on the detector for sphere n
Pkyn1: Y position of the sphere n at rotation angle 0°
Pkyn2: Y position of the sphere n at rotation angle 180°
M1: Average magnification at rotation angle 0°
M2: Average magnification at rotation angle 180°

Further inventive features of the invention can be seen in FIG. 3 to 5. FIG. 3 represents a purely schematic diagram of a coordinate measuring device 110 with a housing 112, which comprises a base plate 114, a rear wall 116, side walls 118, 120 as well as a top wall 122, which can also be identified as a cover plate.

The x-axis, y-axis and z-axis of the coordinate measuring device are labeled in the drawing with the reference numbers 124, 126 and 128. On the inside 130 of the rear wall 116 of the housing 112 a guide runs in the direction X, adjustably mounted along which, hence running in the direction X 124, is a mounting 132 for a rotating table 134, on which the object 136 to be measured is arranged. In other words, the rotating table 134 is arranged on the x-axis 124.

Running along the y-axis 126 are guides, along which a housing 138 can be displaced. Projecting from the housing 138 is a mounting 140 that is displaceable along the z-axis 128.

Furthermore, projecting from the base plate 114 is an x-ray source 142, the x-rays of which penetrate the object 136 arranged on the rotating table 134. The x-rays are captured by suitable sensors such as CCD sensors that are sensitive to x-rays.

Furthermore, sensors 144 can project from the z-axis 128, specifically from the mounting 140 in the embodiment. The sensors here can be those that are conventional for coordinate measuring devices, hence, for example, tactile or optical sensors. Thus not only tomography can be performed, but tactile or optical measurements can also be made with image-processing sensors, laser distance sensors etc.

Due to the use of x-rays, it is required that the coordinate measurement device 110 be provided with sufficient shielding to prevent outward escape. In this regard the invention proposes that at least several of the weight-bearing components provide a shielding function. For example, the base plate 114 and/or the rear wall 116 can be dimensioned or designed to ensure the required shielding function.

At the same time, the corresponding walls 114, 116 thereby provide a function that is required for the measurement technology assembly, namely a guide for the x- and y-axes in the embodiment.

It is also possible to provide walls that do not feature a sufficient shielding effect with radiation absorbing layers 146 on the inside and/or the outside. In this particular case, lead sheeting is involved.

With regard to the weight-bearing walls, in particular those providing a shielding function, the use of hard stone such as granite or appropriate materials is preferred. Also conceivable for use is an artificial hard stone such as polymer concrete, which can be treated with x-ray-absorbing material such as magnetite or similar to the degree required.

According to the invention, the housing 112 of the coordinate measuring device or parts thereof perform a double function, namely that of the required shielding as well as that of serving as functional components of the measurement technology assembly. This results in a compact construction.

To allow high measurement density or to facilitate only short radiation exposure times at each measurement position without sacrificing measurement accuracy, it is provided according to FIG. 4 that multiple tomograms are taken simultaneously—thus in each measurement position of the object 136—at different irradiation angles. In FIG. 4 projecting from the base plate 114 is the rotating table 134 as is shown in FIG. 3, on which an object (not shown) to be measured is arranged, which is irradiated by x-radiation 150 emanating from a x-ray generator 148. In the embodiment, the radiation is captured by a total of three x-ray sensors 152, 154, 156, so that three tomograms for different irradiation directions in a single measurement position of the object are yielded. In each measurement position, hence each angular position of the rotating table 34, the sensors 152, 154, 156 are read out and projection images for the tomogram are acquired. The angular position of the sensors 152, 154, 156 is designed in such a way that each angle between the sensors 152, 154, 156 differs by a whole number multiple of the rotating table 136 angular step used in operating the computer tomograph, while the second and third sensor 154, 156 are arranged as rotated by one third of the angular step in relation to the first sensor 152 and the second sensor 154, respectively.

To take more tomograms of the object 136 to be measured, where the angle between the rotation axis 158 of the rotating table 154 and the x-radiation 150 is visibly changed, three sensors 160, 162 164 are arranged, for example, at different angles to the main irradiation direction of the x-ray source 148 in the embodiment shown in FIG. 5, whereby the visible deviation of the x-rays source in relation to the rotation axis 158 is simulated.

The double arrow 166 drawn in FIG. 5 is intended to symbolize that the rotating table 134 can be adjusted along the rotation axis 158 parallel to the X-axis.

FIG. 9 schematically illustrates that, during the process of tomography, a calibration body, preferably in the form of spheres 300, 302, can, in principle, be tomographically imaged at the same time, thereby yielding the relative position of the rotation axis 158 of the rotating table 134 on which the object 136 to be measured is arranged. The spheres 300, 302 can be arranged in a housing 304 of low x-ray absorption, whereas the spheres 300, 302 are highly absorbent and are made of steel, for example. During the process of tomography, the position of the rotation axis 158 in relation to the coordinate measuring device or to the x-ray source 10 or to the sensor 7 can be determined without any problems before then being mathematically corrected.

According to the invention, measurement points on the object of measurement are gathered with a tactile and/or optical sensor system and used in the correction of the measurement points gathered with the x-ray sensor system. This is should become clear from FIG. 11, which illustrates the principle of a corresponding correction procedure. FIG. 11 shows an object of measurement 400 that is measured tactilely and optically at selected points. In this example, corresponding measurement points are labeled with the reference numbers 402, 404, 406. In the process of tomographic imaging, which is performed subsequently in the same coordinate measuring device, the form, as changed through typical errors of tomography, appears in the tomographic point cloud 408. This can be due to typical tomography artifacts, for example. The positions of the tomographic measurement points are corrected on the basis of the available measurement points measured more precisely with optical and/or tactile sensor system and illustrated once again in FIG. 11b. Interpolation can be performed between the tactilely and optically measured measurement points. The result obtained is then a geometrically corrected tomographically measured point cloud 410 that better corresponds to the form of the object of measurement 400 than does the original data of the tomogram. This point is illustrated through a comparison of 11b and 11c.

During the processes of performing the measurements and analyzing the measurement results, the image-processing sensor system for measuring the visible light in the transmitted light method—if necessary also in the incident light method—can be coupled to the same image processing evaluation unit or the same image processing board as the x-ray sensor system. Driven by software, it is then possible to switch between both of the sensors and digitalize and compute in the same hardware. This is conceptually illustrated in FIG. 10, in which an image-processing sensor system 500 and an x-ray sensor system 502 are connected to the same image processing board 502 so that they may function in the manner described above.

The invention claimed is:

1. A multisensor coordinate measuring device for measuring points on a surface of a workpiece, said device comprising:
    an x-ray computer tomography sensor system as a first sensor system for acquiring three-dimensional datasets of said workpiece, and comprising an x-ray source and at least one x-ray sensor; and
    a tactile and/or optical sensor system as a second sensor system, integrated within the multisensor coordinate measuring device and movable relative to the workpiece in x-, y- and/or z-direction;
    wherein the first sensor system and the second sensor system measure the points on the surface of the workpiece by using a common coordinate system;
    wherein the x-ray and tactile and/or optical sensor systems are movable relative to each other and to the workpiece; and
    wherein the workpiece is rotatable 360° relative to the x-ray system about a rotation axis that is perpendicular to the measuring beam direction of the x-ray computer tomography sensor system; and
    wherein for the measuring of the workpiece, n-sensors simultaneously struck by x-rays are assigned to the x-ray source, and wherein the x-ray source is adjusted between consecutively performed measurements relative to the workpiece at a base angle α, and wherein sensors arranged one after the other are aligned, twisted, or tilted relative to each other at an angle α/n.

2. A coordinate measuring device according to claim 1, wherein the x-ray sensor system and the second sensor system are arranged so that the x-ray sensor is movable relative to the workpiece in x-, y- and/or z-direction of the multisensor coordinate measuring device.

3. A multisensor coordinate measuring device according to claim 1, wherein the x-ray sensor system is arranged on a common mechanical axis with at least the tactile sensor system and/or the optical sensor system.

4. A multisensor coordinate measuring device according to claim 3, wherein the workpiece is rotatable about a rotation axis that is perpendicular to the measuring beam direction of the x-ray sensor system and/or the optical sensor system.

5. A multisensor coordinate measuring device according to claim 4, wherein the rotation axis rotates on a vertically running axis.

6. A multisensor coordinate measuring device according to claim 4, wherein the optical axis for the optical sensor and/or the ray axis for the x-ray sensor is horizontal and/or perpendicular to the rotation axis.

7. A multisensor coordinate measuring device according to claim 4, wherein several sensors are arranged along a straight line running parallel to the rotation axis of the workpiece and are arranged in relation to the projection axis of the x-ray source at angles deviating from one another.

8. A multisensor coordinate measuring device according to claim 4, wherein the rotation axis of the workpiece is arranged on a traveling axis for expanding the measurement range along the rotation axis.

9. A multisensor coordinate measuring device according to claim 4, wherein the workpiece is arranged on a rotating table rotatable around the rotating axis, wherein arranged in the rotating table or in an element immediately connected thereto, is a calibration body, which is arranged in a material that features lower x-ray absorption than the calibration body itself.

10. A multisensor coordinate measuring device according to claim 1, wherein the x-ray sensor system is arranged on a separate mechanical axis, wherein the mechanical axis of the x-ray sensor functions in the same way as the mechanical axes do for the tactile and/or optical sensor system.

11. A multisensor coordinate measuring device according to claim 1, wherein the second sensor system is an optical sensor system using image processing, and wherein radiation or a light source for the x-ray sensor system and/or the optical sensor system is moved synchronously with the assigned sensor.

12. A multisensor coordinate measuring device according to claim 11, wherein the optical sensor system using image-processing and x-ray sensor system are connected to a common image processing evaluation unit or image processing board.

13. A multisensor coordinate measuring device according to claim 1, wherein the device comprises a coordinate system wherein the x-ray source for the x-ray sensor system is fixedly arranged relative to the coordinate system.

14. A multisensor coordinate measuring device according to claim 1, wherein both the x-ray sensor system and the second sensor system are positionally adjusted in relation to the workpiece along at least one axis.

15. A multisensor coordinate measuring device according to claim 1, wherein both the x-ray sensor system and the second sensor system are positionally adjusted in relation to the workpiece along at least two axes.

16. A multisensor coordinate measuring device according to claim 1, wherein both the x-ray sensor system and the second sensor system are positionally adjusted in relation to the workpiece along at least three axes.

17. A multisensor coordinate measuring device according to claim 1, wherein at least one additional sensor is adjusted synchronously with the x-ray sensor system.

18. A multisensor coordinate measuring device according to claim 1, wherein a measurement area adaptation is achieved automatically by adjusting the distance between the x-ray sensor and the x-ray source and/or by adjusting the x-ray sensor system relative to the workpiece.

19. A multisensor coordinate measuring device according to claim 1, wherein the x-rays are shielded or partially shielded.

20. A multisensor coordinate measuring device according to claim 19, wherein a base plate and/or at least one side or rear wall of the multisensor coordinate measuring device acts as shielding.

21. A multisensor coordinate measuring device according to claim 19, wherein the shielding components are made of stone.

22. A multisensor coordinate measuring device according to claim 19, wherein one or more components of the multisensor coordinate measuring device are mounted on the shielding components.

23. A multisensor coordinate measuring device according to claim 22, wherein the shielding is the mounting site or area for at least one mechanical axis or a traveling axis and/or mounting and/or guide for an element.

24. A multisensor coordinate measuring device according to claim 1, wherein a plurality of sensors is assigned to the x-ray source, wherein the irradiation angles of the x-rays penetrating the workpiece deviate from one another, and wherein the sensors are arranged at different angles to a main irradiation direction of the x-ray source.

25. A multisensor coordinate measuring device according to claim 1, wherein a plurality of sensors detecting the x-rays is used, wherein the sensors are arranged at different angles to a main irradiation direction of the x-ray source, so that for each sensor, an x-ray image of the workpiece is taken at a different irradiation angle.

26. A multisensor coordinate measuring device according to claim 1, wherein tomograms of the workpiece are obtained by using different spectral ranges of the x-rays.

27. A multisensor coordinate measuring device according to claim 1, wherein during measurement, the workpiece is continuously rotated and discontinuously exposed to x-rays.

28. A multisensor coordinate measuring device according to claim 1, wherein a mechanical and/or electronic shutter is assigned to an outlet of the x-ray source.

29. A multisensor coordinate measuring device according to claim 1, wherein high frequency x-radiation is used.

30. A multisensor coordinate measuring device according to claim 1, wherein an workpiece exhibiting low contrast relative to x-rays is surrounded or encased by a material with an x-ray absorption greater than that of the workpiece.

31. A multisensor coordinate measuring device according to claim 1, further comprising sensors for detecting and measuring the workpiece.

32. A multisensor coordinate measuring device according to claim 1, wherein at least one sensor is arranged on separate traveling or mechanical axes.

33. A method for calibrating an x-ray sensor system in a multisensor coordinate measuring device according to claim 1, wherein:
    marked points on the surface of the workpiece to be measured are measured with a tactile or optical sensor system and geometrical features are ascertained for calibrating the x-ray sensor system; and
    the measurement results obtained through the tactile and/or optical sensor system are used for correction of a measured point cloud generated from 3D-voxel-data, said measured point cloud being generated by threshold methods and the 3D-voxel-data resulting from the measuring with the x-ray sensor system.

34. A method according to claim 33, wherein measurement results for the marked points through tactile and/or optical sensor systems are obtained before computation of the 3D-reconstruction of the x-ray procedure.

35. A method according to claim 33, wherein measurement points alternatively ascertained with tactile sensor systems, optical sensor systems or x-ray sensor systems are analyzed in a common coordinate system.

36. A method according to claim 33, wherein the geometrical features are calculated from points measured by a combination of x-ray sensor systems, optical sensor systems or tactile sensor systems.

37. A method according to claim 33, wherein a common point cloud for further analysis is generated from the measurement points obtained with the x-ray sensor system and from measurement points obtained with the tactile sensor system, or from measurement points obtained with the x-ray sensor system and from measurement points obtained with the optical sensor system.

38. A multisensor coordinate measuring device for measuring points on a surface of a workpiece, said device comprising:
    an x-ray computer tomography sensor system as a first sensor system for acquiring three-dimensional datasets of said workpiece, and comprising an x-ray source and at least one x-ray sensor; and
    a tactile and/or optical sensor system as a second sensor system, integrated within the multisensor coordinate measuring device and movable relative to the workpiece in x-, y- and/or z-direction;
    wherein the first sensor system and the second sensor system measure the points on the surface of the workpiece by using a common coordinate system;
    wherein the x-ray and tactile and/or optical sensor systems are movable relative to each other and to the workpiece;

wherein the workpiece is rotatable 360° relative to the x-ray system about a rotation axis that is perpendicular to the measuring beam direction of the x-ray computer tomography sensor system;

wherein marked points on the surface of the workpiece to be measured are measured with a tactile or optical sensor system and geometrical features are ascertained for calibrating the x-ray sensor system; and wherein the measurement results obtained through the tactile and/or optical sensor system are used for correction of a measured point cloud generated from 3D-voxel-data, said measured point cloud being generated by threshold methods and the 3D-voxel-data resulting from the measuring with the x-ray sensor system.

39. A coordinate measuring device according to claim 38, wherein the x-ray sensor system and the second sensor system are arranged so that the x-ray sensor is movable relative to the workpiece in x-, y- and/or z-direction of the multisensor coordinate measuring device.

40. A multisensor coordinate measuring device according to claim 38, wherein the x-ray sensor system is arranged on a common mechanical axis with at least the tactile sensor system and/or the optical sensor system.

41. A multisensor coordinate measuring device according to claim 40, wherein the workpiece is rotatable about a rotation axis that is perpendicular to the measuring beam direction of the x-ray sensor system and/or the optical sensor system.

42. A multisensor coordinate measuring device according to claim 41, wherein the rotation axis rotates on a vertically running axis.

43. A multisensor coordinate measuring device according to claim 41, wherein the optical axis for the optical sensor and/or the ray axis for the x-ray sensor is horizontal and/or perpendicular to the rotation axis.

44. A multisensor coordinate measuring device according to claim 41, wherein several sensors are arranged along a straight line running parallel to the rotation axis of the workpiece and are arranged in relation to the projection axis of the x-ray source at angles deviating from one another.

45. A multisensor coordinate measuring device according to claim 41, wherein the rotation axis of the workpiece is arranged on a traveling axis for expanding the measurement range along the rotation axis.

46. A multisensor coordinate measuring device according to claim 41, wherein the workpiece is arranged on a rotating table rotatable around the rotating axis, wherein arranged in the rotating table or in an element immediately connected thereto, is a calibration body, which is arranged in a material that features lower x-ray absorption than the calibration body itself.

47. A multisensor coordinate measuring device according to claim 38, wherein the x-ray sensor system is arranged on a separate mechanical axis, wherein the mechanical axis of the x-ray sensor functions in the same way as the mechanical axes do for the tactile and/or optical sensor system.

48. A multisensor coordinate measuring device according to claim 38, wherein the second sensor system is an optical sensor system using image processing, and wherein radiation or a light source for the x-ray sensor system and/or the optical sensor system is moved synchronously with the assigned sensor.

49. A multisensor coordinate measuring device according to claim 48, wherein the optical sensor system using image-processing and x-ray sensor system are connected to a common image processing evaluation unit or image processing board.

50. A multisensor coordinate measuring device according to claim 38, wherein the device comprises a coordinate system wherein the x-ray source for the x-ray sensor system is fixedly arranged relative to the coordinate system.

51. A multisensor coordinate measuring device according to claim 38, wherein both the x-ray sensor system and the second sensor system are positionally adjusted in relation to the workpiece along at least one axis.

52. A multisensor coordinate measuring device according to claim 38, wherein both the x-ray sensor system and the second sensor system are positionally adjusted in relation to the workpiece along at least two axes.

53. A multisensor coordinate measuring device according to claim 38, wherein both the x-ray sensor system and the second sensor system are positionally adjusted in relation to the workpiece along at least three axes.

54. A multisensor coordinate measuring device according to claim 38, wherein at least one additional sensor is adjusted synchronously with the x-ray sensor system.

55. A multisensor coordinate measuring device according to claim 38, wherein a measurement area adaptation is achieved automatically by adjusting the distance between the x-ray sensor and the x-ray source and/or by adjusting the x-ray sensor system relative to the workpiece.

56. A multisensor coordinate measuring device according to claim 38, wherein the x-rays are shielded or partially shielded.

57. A multisensor coordinate measuring device according to claim 56, wherein a base plate and/or at least one side or rear wall of the multisensor coordinate measuring device acts as shielding.

58. A multisensor coordinate measuring device according to claim 56, wherein the shielding components are made of stone.

59. A multisensor coordinate measuring device according to claim 56, wherein one or more components of the multisensor coordinate measuring device are mounted on the shielding components.

60. A multisensor coordinate measuring device according to claim 59, wherein the shielding is the mounting site or area for at least one mechanical axis or a traveling axis and/or mounting and/or guide for an element.

61. A multisensor coordinate measuring device according to claim 38, wherein a plurality of sensors is assigned to the x-ray source, wherein the irradiation angles of the x-rays penetrating the workpiece deviate from one another, and wherein the sensors are arranged at different angles to a main irradiation direction of the x-ray source.

62. A multisensor coordinate measuring device according to claim 38, wherein a plurality of sensors detecting the x-rays is used, wherein the sensors are arranged at different angles to a main irradiation direction of the x-ray source, so that for each sensor, an x-ray image of the workpiece is taken at a different irradiation angle.

63. A multisensor coordinate measuring device according to claim 38, wherein tomograms of the workpiece are obtained by using different spectral ranges of the x-rays.

64. A multisensor coordinate measuring device according to claim 38, wherein during measurement, the workpiece is continuously rotated and discontinuously exposed to x-rays.

65. A multisensor coordinate measuring device according to claim 38, wherein a mechanical and/or electronic shutter is assigned to an outlet of the x-ray source.

66. A multisensor coordinate measuring device according to claim 38, wherein high frequency x-radiation is used.

67. A multisensor coordinate measuring device according to claim 38, wherein a workpiece exhibiting low contrast relative to x-rays is surrounded or encased by a material with an x-ray absorption greater than that of the workpiece.

68. A multisensor coordinate measuring device according to claim 38, further comprising sensors for detecting and measuring the workpiece.

69. A multisensor coordinate measuring device according to claim 38, wherein at least one sensor is arranged on separate traveling or mechanical axes.

70. A method according to claim 38, wherein measurement results for the marked points through tactile and/or optical sensor systems are obtained before computation of the 3D-reconstruction of the x-ray procedure.

71. A method according to claim 38, wherein measurement points alternatively ascertained with tactile sensor systems, optical sensor systems, or x-ray sensor systems are analyzed in a common coordinate system.

72. A method according to claim 38, wherein the geometrical features are calculated from points measured by a combination of x-ray sensor systems, optical sensor systems, or tactile sensor systems.

73. A method according to claim 38, wherein a common point cloud for further analysis is generated from the measurement points obtained with the x-ray sensor system and from measurement points obtained with the tactile sensor system, or from measurement points obtained with the x-ray sensor system and from measurement points obtained with the optical sensor system.

* * * * *